United States Patent [19]

Belanus et al.

[11] Patent Number: 6,060,086
[45] Date of Patent: May 9, 2000

[54] METHODS OF USING RECYCLED DRYWALL

[75] Inventors: Ted Belanus; James Kramer, both of Brooklyn, Wis.

[73] Assignee: Gypsum Recycling, Inc., Brooklyn, Wis.

[21] Appl. No.: 08/856,953

[22] Filed: May 15, 1997

[51] Int. Cl.[7] ............................ A01N 59/06; A01N 59/00; A01N 43/04
[52] U.S. Cl. ........................... 424/686; 424/687; 424/696; 424/724; 514/57
[58] Field of Search ..................... 424/696, 686, 424/687, 724; 514/51; 71/121; 119/670

[56] References Cited

U.S. PATENT DOCUMENTS

| | | |
|---|---|---|
| 250,352 | 12/1881 | Haggin et al. . |
| 398,527 | 2/1889 | Miller . |
| 435,509 | 9/1890 | Mann ........................................ 424/696 |
| 460,227 | 9/1891 | Wheeler .................................. 119/172 |
| 1,001,852 | 8/1911 | Hutchinson . |
| 1,186,564 | 6/1916 | Fest ........................................... 241/23 |
| 1,254,908 | 1/1918 | Holton . |
| 1,336,957 | 4/1920 | Hedenburg . |
| 4,163,674 | 8/1979 | Been ................................... 106/15.05 |
| 4,278,047 | 7/1981 | Luca ........................................... 119/1 |
| 4,315,761 | 2/1982 | Larrson et al. ............................. 71/21 |
| 4,405,354 | 9/1983 | Thomas, II et al. ....................... 71/21 |
| 4,510,019 | 4/1985 | Bartelloni ................................ 162/141 |
| 4,676,196 | 6/1987 | Lojek et al. ................................. 119/1 |
| 4,721,659 | 1/1988 | Tieckelmann et al. ................. 428/701 |
| 4,917,802 | 4/1990 | Fukaya et al. .......................... 210/605 |
| 4,925,826 | 5/1990 | Hamm et al. ........................... 502/407 |
| 4,971,796 | 11/1990 | Sjogren .................................. 424/417 |
| 4,983,390 | 1/1991 | Levy ....................................... 424/404 |
| 4,994,113 | 2/1991 | Helmstetter ............................ 106/618 |
| 5,053,446 | 10/1991 | Salyer ......................................... 524/8 |
| 5,100,063 | 3/1992 | Bauer ......................................... 241/14 |
| 5,171,366 | 12/1992 | Richards et al. ........................ 106/780 |
| 5,183,213 | 2/1993 | Knez, Jr. ................................... 241/24 |
| 5,215,041 | 6/1993 | Krahenbuhl ............................ 119/172 |
| 5,238,195 | 8/1993 | Knez, Jr. ................................... 241/24 |
| 5,401,588 | 3/1995 | Garvey et al. .......................... 428/703 |
| 5,433,388 | 7/1995 | Hirz et al. ................................ 241/23 |

*Primary Examiner*—Jose'G. Dees
*Assistant Examiner*—Alton Pryor
*Attorney, Agent, or Firm*—Michael Best & Friedrich LLP

[57] ABSTRACT

The invention relates to a method of using recovered drywall to achieve an effect in an animal habitat. The method includes applying an amount of recovered drywall to surfaces of the habitat, the effect achieved being reduction or control of bacterial count, fly population, odor or combinations thereof.

14 Claims, No Drawings

METHODS OF USING RECYCLED DRYWALL

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

This invention relates to methods of utilizing recovered drywall, and in particular, to the use of recovered drywall to reduce insect population in animal habitats, such as dairy barns, and to reduce microbial, e.g., bacterial population in such structures and particularly on animal surfaces, as well as to reduce animal habitat odor.

It has been estimated that 12–27% of construction and demolition debris is waste drywall. For single family construction, it is estimated that there is about 1–1.5 lbs. of drywall waste per square foot of floor area, e.g., construction of a 2000 sq. ft. may yield up to 3000 lbs. of waste or scrap wallboard. As such, waste drywall is the second largest source of waste, second only to wood. As with most waste or scrap, the community landfills are the ultimate resting place for waste drywall; some landfills, however, have already banned landfilling of gypsum drywall.

The terms "drywall", "wallboard", "sheetrock", "building board", "plasterboard" or "gypsum board" as used herein and generally in the industry, refer to a prefabricated substantially rectangular walling material which is of sandwich construction, i.e., a hardened gypsum-based plaster core or slab sandwiched between fibrous material, e.g., paper, facings or cover sheets. Gypsum is the most common of the naturally occurring sulfate minerals, and a calcium sulfate hydrate (i.e., 79% calcium sulfate and 21% water), $CaSO_4H_2O$. The composition of a typical gypsum-based wallboard is about 75–95% gypsum, 3–9% paper, 1% fiberglass, 0.3–1% starch and the remainder, a combination of organic binders, adhesives, dispersants, and water resistant additives. It is noted that unfaced gypsum board is also known; see, e.g., U.S. Pat. No. 5,171,366 issued to Richards et al.

Recently, various methods of processing the waste or scrap drywall to separate the gypsum-based core and the backing paper are known. See, e.g., U.S. Pat. No. 5,100,063 issued to Bauer; U.S. Pat. No. 5,183,213 and 5,238,195 issued to Knez; U.S. Pat. No. 5,433,388 issued to Hirz et al.

The recovered gypsum-based core has been used to re-manufacture drywall. However, some agricultural uses have been reported. Most of these uses of the recovered core material parallel the uses of virgin gypsum, e.g., soil amendment to neutralize alkaline and saline soils, to improve the permeability of argillaceous materials, to provide sulfur and calcium for plants, to remediate soils high in sodium and to reduce soil crusting.

As with all waste materials, there is a need for finding other uses for the recovered product. The need for such uses is no greater than in the drywall area considering the large amounts of waste wallboard created each year.

BRIEF SUMMARY OF THE INVENTION

The present invention provides a method for using recovered drywall for certain animal farming conditions. Specifically, it has been found that recovered drywall is of use in reducing fly populations in animal habitats, e.g., barns, in reducing or controlling odors, especially animal habitat odors, and in controlling or reducing somatic cell and bacterial counts on livestock.

The foregoing, and other advantages of the present invention, are realized in one aspect thereof in a method for using recovered drywall which includes applying the drywall to the surfaces of an animal habitat to reduce or inhibit the growth of insects, particularly flies. The drywall is suitably applied to the surfaces, e.g., the walls and floor, in a fine and even distribution in the form of a powder or a slurry.

In another aspect, the invention provides a method for reducing bacterial and somatic cell counts on animal habitat surfaces, particularly animal surfaces, e.g., the teats of a cow, by applying recovered drywall to the animal surface. The drywall is suitably applied in a powdered form and is suitably dusted directly on the animal surface.

In yet another aspect, the invention provides a method for odor control, especially in an animal habitat, by applying recovered drywall to the surfaces of the animal habitat, e.g., barn, or mixing the drywall with animal excreta, e.g., manure, thereby inhibiting ammonia or nitrogenous substance release. The drywall is suitably applied in powder form or slurry form.

In a further aspect, the invention provides a method for reducing the incidence of scours in young calves and pigs by providing recovered drywall to the young animals in the form of application to the surfaces of the living space of the animals.

Other advantages and a fuller appreciation of specific variations and attributes of the present invention will be gained upon an examination of the following detailed description of preferred embodiments, taken in conjunction with the appended claims.

BRIEF DESCRIPTION OF THE DRAWING(S)

Not Applicable

DETAILED DESCRIPTION OF THE INVENTION

The present invention provides a method for the using recovered drywall in animal farming applications. Particularly, the present invention relates to a method for reducing or inhibiting insect population, particularly fly population. It also relates to a method of reducing or controlling the somatic cell and bacterial count on livestock, particularly the teats of dairy cows, and animal habitat surfaces, and for odor control, particularly in animal habitats.

In the following description of the method of the invention, process steps are carried out at ambient temperatures and atmospheric pressure.

As used herein, the term "recovered drywall" is meant to refer to the gypsum-based core portion of plasterboard with or without the paper facing of finished plasterboard products.

In accordance with the present invention, when effective amounts of recovered drywall are applied to animal habitat (e.g., barns) surfaces, the proliferation of fly population is reduced or inhibited. Similarly, the somatic cell and bacterial count of animal skin is reduced, thereby being effective in the prevention of mastitis. There is also a significant reduction in odor from the habitat and/or animals therein.

The recovered drywall is suitably applied in the form of a powder or slurry. The recovered drywall is dusted, spread or sprayed on the surfaces sought to be treated, typically floor and wall areas, at a concentration of about 3–10 g/sq. ft., preferably about 5 g/sq. ft. of surface area. In all applications, the best results are obtained if there is a fine and uniform distribution of the recovered drywall on the surface area of the barn, or in the case, of odor control or reduction, the recovered drywall can be mixed with manure at a concentration of about 10 g/pound of manure.

Although the recovered drywall is absorbent, it has been found that the recovered drywall does not support environmental microbial growth.

The recovered drywall is produced in a known manner, for example, by crushing the drywall between rollers, and then, optionally screening out the paper from the core material, generally leaving only about 1–2% paper in the recovered core material. See, e.g., U.S. Pat. Nos. 5,100,063, 5,183,213, 5,238,195, and 5,433,388, all of which are incorporated herein by reference. The composition of the recovered drywall can vary according to the composition of the fabricated product from which is recovered, which varies from manufacturer to manufacturer. Generally, the composition of the recovered drywall (with paper facing screened out) is by weight about 65–98% gypsum; about 1–2% glass fiber; about 1–2% cellulose fiber. A particularly useful recovered drywall material was found to have a composition by weight of 65–75% gypsum; 20–30% calcite; 2–5% quartz; 1–2% glass fiber; and 1–2% cellulose fiber. It is noted that while gypsum is the major component, recovered drywall is a composition of several components. It is also, however, expressly understood that the use of virgin gypsum in place of recovered drywall in the methods of the present invention is within the scope of the present invention.

As described hereinabove, the recovered drywall is applied suitably as a powder or as a slurry to the surfaces of the animal habitat and/or the animal, to liquid manure lagoons or pits, or mixed directly with solid manure in the animal habitat.

For mastitis prevention, the recovered drywall is suitably applied with, e.g., a powder puff, to the teats of the cows. When applied directly, the recovered drywall is applied at a concentration of about 0.01 to 0.04 g/sq. in.

For odor control or reduction, the recovered drywall is applied in powder or slurry form to the surfaces of the animal habitat, or mixed directly with solid manure in the animal habitat. The recovered drywall can also be applied directly to liquid manure lagoons or pits to provide odor control to a broader environment. In a lagoon or pit application, the recovered drywall can be spread or distributed over the manure in the lagoon or pit. It has been found that the recovered drywall inhibits the release of ammonia and other nitrogeneous substances, thereby reducing or eliminating, in some cases, the odor associated therewith. Such substances are atmospheric irritants and their reduction or elimination improves environmental quality and animal respiration.

The recovered drywall of the present invention is also contemplated to be of value in preventing or reducing the occurrence of scours, a life-threatening diarrheal disease in newborn pigs and calves which has been reported to occur in about 30% of newborns. It was found at one experimental farm site that the incidence of scours in newborn pigs was reduced by about 95% by use of recovered drywall on the surfaces of the animal habitat.

The present invention is further explained by the following examples which should not be construed by way of limiting the scope of the present invention.

EXAMPLE 1

All floor and wall surfaces of two dairy barn stalls (typically, about 6 ft×4 ft) were dusted with recovered drywall at a concentration of 5 g/sq. ft. A cow was stalled in the usual manner in each stall. After 5 days, the first cow was changed to a stall in which barn lime but no recovered drywall had been dusted. The second cow continued in the drywall dusted stall.

Sampling for teat end microbial counts was performed as follows: Prior to milking, teat ends of the cow were swabbed with a clean room (½ in square) sponge which had been autoclaved and dipped in a phosphate buffer. After swabbing, each sponge was placed in a plastic bag containing a known amount of sterile tryptic soy broth (2–10 mL). The sponges were agitated and/or vortexed in the bags. Samples from each bag were cultured on blood agar plates (tryptic soy broth, agar and 5% defibrinated sheeps' blood) and incubated overnight at 37° C. Bacterial colonies were counted for each plate.

For each sampling, six successive swabs were taken for each cow as well as a post-milking swab. In the post-milking swab, the milking machine was removed from the cow teats, then the teat end was dipped in an iodine solution. The teat end was then swabbed as described above and the sponge swab was immersed in a sterile tryptic soy broth. The teat end was then again dipped in the iodine solution. The entire test period of sampling swabbing was 15 days.

The following data were collected:

TABLE 1

| Average Bacterial Count for First Swab Culture | | | |
| --- | --- | --- | --- |
| | COW #1 | COW #2 | COW #2 |
| colony forming units (cfu) | 39,542[a] | 50,050[b] | 930,734[c] |

[a] = cow stall treated with recovered drywall for entire test period.
[b] = cow stall treated with recovered drywall for 5 days.
[c] = cow stall treated with barn lime for 10 days.

These data showed that the bacterial teat end count of the cow whose stall was dusted with recovered drywall was significantly less than for the cow placed in a stall dusted with barn lime. As bacterial count is an index of mastitis, a bacterial infection of the mammary gland that prevents cows from producing milk, the reduction of bacterial count with recovered drywall treatment indicates that such treatment is of value in preventing mastitis.

EXAMPLE 2

Manure was collected from the floor of two farrowing crates of pigs, one of which had been dusted with recovered drywall, the other was not so treated. Samples of the manure from each crate were placed in two 5-gallon buckets and the buckets were half-filled. An added dusting of recovered drywall was added to the manure collected from the recovered drywall dusted crate. Each bucket was fitted around the perimeter with a nylon hosiery material which material had a leg opening that could be tied off so that the top of each bucket was covered. Thus, each bucket was covered by the mesh of the nylon material such that flies, once hatched, could not escape. One set of buckets (i.e., one from the treated crate and one from the untreated create) was placed outdoors in an area of many flies for 24 hours. The other set were placed indoors in a room in which the temperature varied between about 70° F. and 80° F. 60 mL of tap water was added daily to each bucket to prevent dessication of any fly eggs. When flies began to appear, the leg portion was opened once daily and connected to a vacuum having collection screen. The flies were vacuumed up, allowed to die and counted.

Flies appeared in the buckets having the untreated manure in about 4 days. No flies appeared in the buckets with recovered drywall treated manure until 7 days. After 15 days, the fly count in treated manure was 2% of the fly count for the corresponding bucket with untreated manure.

EXAMPLE 3

A second fly study was conducted collecting manure from pig farrowing crates in the same manner as described in Example 2. The same procedure as described in Example 2 was also followed to count fly population. Flies appeared in the bucket with untreated manure after 10 days and in the bucket with drywall-treated manure after 14 days. After 20 days, the fly-count for the bucket with drywall-treated manure was 2% of that for the bucket with untreated manure.

EXAMPLE 4

A third fly study was conducted collecting manure from pig farrowing crates in the same manner as described in Example 2. The same procedure as described in Example 2 was also followed to count fly population. Flies appeared in the bucket with untreated manure after 6 days and in the bucket with drywall-treated manure after 9 days. After 16 days, the fly-count for the bucket with drywall-treated manure was 22% of that for the bucket with untreated manure.

EXAMPLE 5

A fourth fly study was conducted collecting manure from pig farrowing crates as described in Example 2. After 22 days, the fly count for the bucket with drywall-treated manure was 3% of that for the bucket with untreated manure.

These studies show that recovered drywall is effective in reducing or slowing the growth and development of flies in animal habitat environments. Such results are truly surprising and would not have been expected by following the teachings of the prior art.

EXAMPLE 6

A study is conducted in which the teats of 50 cows of a herd are dusted daily with recovered drywall for three weeks. A control group of 50 cows has no treatment. Teats of the cows of both groups are swabbed daily and bacterial counts are determined as described in Example 1. The results show a reduced incidence of mastitis in the cows treated with recovered drywall compared to the control cows that received no treatment.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

We claim:

1. A method of using recovered drywall to achieve an effect in an animal habitat comprising, applying an effective amount of recovered drywall in a concentration of about 3–10 g/sq. ft. to surfaces of the habitat, wherein the effect is reduction in bacterial count, reduction in fly population, reduction in odor or a combination thereof, and wherein said recovered drywall is applied as a powder or a slurry.

2. The method of claim 1, wherein said effect is a reduction of bacterial count.

3. A method of using recovered drywall to achieve an effect in a habitat of an animal comprising, applying an effective amount of recovered drywall in a concentration of about 3–10 g/sq. ft. to surfaces of the habitat or the animal or both, wherein the effect is reduction in bacterial count, reduction in fly population, reduction in odor or a combination thereof, and wherein the animal is a cow and said recovered drywall is applied to the teats of the cow.

4. The method of claim 1, wherein said effect is a reduction of fly population.

5. The method of claim 1, wherein said effect is a reduction in odor.

6. The method of claim 4, wherein said drywall is further applied to animal excreta in the habitat.

7. A method for treating or reducing the incidence of mastitis in cows comprising, applying an effective amount of recovered drywall to the teats of the cows, wherein said drywall is in powder form and dusted on the teats of the cow.

8. The method of claim 7, wherein said drywall is dusted at a concentration of about 0.01–0.04 g/sq. in.

9. A method of treating an animal habitat to improve the hygenic conditions of the habitat comprising, applying to habitat surfaces recovered drywall in a concentration of about 3–10 g/sq. ft. in an amount sufficient to inhibit or reduce fly population growth, odor, somatic and bacterial cell count or combinations thereof, wherein said recovered drywall is applied as a powder or a slurry.

10. A recovered drywall composition adapted to be used for certain animal farming conditions for any one of different purposes including reduction of fly population, bacterial count on surfaces, and odor, said composition having a drywall paper facing screened out, and said composition comprising 65–98% gypsum, 1–2% glass fiber and 1–2% cellulose fiber and further comprising 20–30% calcite and 2–5% quartz.

11. A recovered drywall composition adapted to be used for certain animal farming conditions for any one of different purposes including reduction of fly population, bacterial count on surfaces, and odor, said composition having a drywall paper facing screened out, said composition comprising 65–75% gypsum, 1–2% glass fiber and 1–2% cellulose fiber and further comprising 20–30% calcite and 2–5% quartz.

12. A method of using recovered drywall by achieving an effect in an animal habitat comprising, applying an effective amount of an agent which is selected from the group consisting of recovered drywall in a concentration of about 3–10 g/sq. ft., gypsum and combinations thereof to surfaces of the habitat, wherein the effect is reduction in bacterial count, reduction in fly population or reduction in odor, wherein said recovered drywall is applied as a powder or a slurry.

13. A method of treating animal excreta to inhibit or reduce odor comprising, treating the excreta with an effective amount of an agent which is selected from the group consisting of recovered drywall, gypsum and combinations thereof wherein said amount is in a concentration of about 10 g/lb of excreta.

14. The method of claim 13, wherein said amount is sufficient to inhibit or reduce the release of ammonia and other nitrogeneous substances from the excreta.

* * * * *